United States Patent [19]

Joos et al.

[11] Patent Number: 5,590,560
[45] Date of Patent: Jan. 7, 1997

[54] APPARATUS FOR MEASURING VISCOSITY OR THICKNESS, SURFACE TENSION AND SURFACE DILATIONAL ELASTICITY

[75] Inventors: Felipe M. Joos, Pittsford, N.Y.; Alfred K. Anders, North Fitzroy, Australia

[73] Assignee: Eastman Kodak Company, Rochester, N.Y.

[21] Appl. No.: 561,904

[22] Filed: Nov. 22, 1995

[51] Int. Cl.$^6$ .................................................. G01M 3/08
[52] U.S. Cl. .......................... 73/64.48; 73/54.01; 356/73
[58] Field of Search ............................... 73/54.01, 54.02, 73/64.48; 356/73

[56] References Cited

U.S. PATENT DOCUMENTS

| | | | |
|---|---|---|---|
| 3,030,802 | 4/1962 | Aarts et al. | 73/64.48 |
| 3,550,433 | 12/1970 | Warburton et al. | 73/54 |
| 3,869,984 | 3/1975 | Toth | 101/349 |
| 4,169,319 | 10/1979 | Gardner | 33/169 |
| 4,512,183 | 4/1985 | Alexander | 73/64.48 |
| 4,674,322 | 6/1987 | Strangeland | 73/54 |
| 4,776,099 | 10/1988 | Euverard | 33/169 |
| 4,884,437 | 12/1989 | Constant et al. | 73/54 |
| 4,953,389 | 9/1990 | Schurch | 73/64.4 |
| 5,024,080 | 6/1991 | Backes | 73/54.01 |
| 5,303,030 | 4/1994 | Abraham et al. | 356/345 |
| 5,317,389 | 5/1994 | Hochberg et al. | 356/382 |

OTHER PUBLICATIONS

Heckl et al, "Electric–field–induced domain movement in phospholipid monolayers", in Thin Solid Films, V. 159, pp. 125–132 (1988).

Lyu and Mudawar "Simultaneous measurements of thickness and temperature profile in a wavy liquid film falling freely on a heating wall", Exp. Ht. Transf. V. 4, pp. 217–233, 1991.

Cross, "Thickness measurements—what do they mean", Pltng. & Surf. Fnshng. Nov. 1979, pp. 22–28.

E. H. Lucassen–Reynders: "Anionic Surfactants: Physical Chemistry of Surfactant Action", Surfactant Science Series, vol. 11, Marcel Dekker, Inc. 1981.

C. H. Soh, K. Miyano and J. B. Ketterson, "Novel technique for dynamic surface tension and viscosity measurements at liquid–gas interfaces", Rev. Sci. Instrum., V. 49, pp. 1669, 1978.

S. J. Weinstein, J. M. Baumlin and J. Servant, "The propagation of surface waves in flow down an oscillating inclined plan", ALChE Journal, V. 39, pp. 1113–1123, 1993.

Joos and Snaddon, "Electrostatically enhanced film condensation", J. of Fluid Mechanics, V. 156, pp. 23–28, 1985.

Soh, Miyano and Ketterson, (Rev. Sci. Instrum., vol. 49(10) Oct. 1978, pp. 1464–1469.

*Primary Examiner*—Hezron E. Williams
*Assistant Examiner*—Jay L. Politzer
*Attorney, Agent, or Firm*—Arthur H. Rosenstein; Mark G. Bocchetti

[57] ABSTRACT

An apparatus and method to measure different properties of a liquid film or coating traveling or resting on a horizontal support, including dynamic viscosity, dynamic surface tension and surface dilational elasticity, the apparatus comprising: a series of wires placed above a moving wet film or coating to which high voltage is applied inducing an electrostatic field that lifts the free surface of said film preferentially near the wires; a means for detecting the free surface displacement of the free surface in the section where the voltage is applied to the coating, possibly the means being a CCD camera coupled to a digital acquisition system; and means for processing the signal to determine the properties of the coating.

8 Claims, 8 Drawing Sheets

APPARATUS FOR MEASURING VISCOSITY OR THICKNESS, SURFACE TENSION AND SURFACE DILATIONAL ELASTICITY

FIELD OF THE INVENTION

This invention relates to an apparatus and method for measuring viscosity or thickness, surface tension and surface dilational elasticity of a wet coating or film on a moving support or web by subjecting the coating to an electrostatic force while measuring the change in thickness with a device such as a CCD camera designed to receive light transmitted through the wet coating or the liquid film. The apparatus can be used on-line in a coating or painting process for purposes of improving the design of setting and drying or their improved control in manufacturing.

BACKGROUND OF THE INVENTION

Knowing the physical properties of fluids, such as dynamic viscosity, local (dynamic) surface tension and surface dilational elasticity is essential when designing fluid processing equipment. Yet these properties vary to a considerable degree depending on the precise operating conditions which the fluid encounters. In particular, the design and operation of setting and drying equipment of coating processing units depend on a knowledge of the physical properties of the process fluids at operating conditions. It is frequently difficult to obtain such data, which varies throughout the setting or drying process. Thus, physical properties, such as viscosity and surface tension are extrapolated from conditions that are very different, and surface dilational elasticity is typically guessed at. Such approaches, however, interject error into the design and operating calculations and create deficiencies in the coating setting and drying processing units. Furthermore, the ability to measure such properties as viscosity of coatings on-line during a coating operation contributes to determining the quality of the coating as it is being manufactured. The present invention, under certain circumstances, can be used to help process quality.

U.S. Pat. Nos. 4,674,322, 3,550,433, 4,953,389, 4,884,437; 5,303,030 and 5,317,387 are illustrative of the prior art relating to the present invention. In U.S. Pat. No. 4,674,322 an instrument for simultaneously measuring viscosity, surface tension and density of a liquid mixed with a gas is disclosed, but it operates on the principle of an harmonic oscillator and cannot be used for thin liquid films. None of the above patents, however, are directed to a method of determining the properties of viscosity and surface tension and surface dilational elasticity of a coating on a support, or perform measurements on thin film. On the other hand, U.S. Pat. No. 3,550,433 describes an apparatus to measure viscosity of drying films by immersing a wire in the liquid film and measuring the tension on the wire as it moves through the film. The principle of the present invention applies electrostatic (and not mechanical) forces and optical or other non-contact (not mechanical) means to measure the liquid film properties.

Heckl et al. "Electric-field-induced domain movement in phospholipid monolayers", in Thin Solid Films, V. 159, pp. 125–132 (1988) describe: an apparatus consisting of a rod electrode positioned perpendicularly to a plate on which a liquid film rests; and a method of measuring, by means of fluorescence microscopy, the radius of the growing circular wave when the electric field is turned on, and determining the viscosity of the film. However, in the apparatus and method described, it appears to be essential that lipid monolayers be present at the free surface, that are attracted or repelled by the electrostatic field, and the equation used to calculate this viscosity depends on such parameters as the size of gel phase domains. In contrast to Heckl et al. the apparatus and method of the present invention are applied to films with properties that are uniform in the plane of the support and the equation used to measure viscosity is completely different and based on different assumptions.

Another aspect of this invention is that, if the viscosity of the coated film is already known (by a means other than this invention), then it is possible to use the invention to measure the thickness of the wet film. U.S. Pat. Nos. 4,169,319 and 4,776,099 offer mechanical means of making this measurement by using, respectively, disks with calibrated notches of different depths and a circular disk that rotates eccentrically. Wet thickness is determined by the location (a notch and angle on the disk, respectively) at which the coating stops wetting the disk. U.S. Pat. No. 3,869,984 teaches a process of controlling wet film thickness that includes predicting film thickness by combining the results of measurements of the splitting and sliding shear forces exerted on a device facing a coating roll, over which the coated support is wrapped and moving, and in which the device wets the coating. Lyu and Mudawar ("Simultaneous measurements of thickness and temperature profile in a wavy liquid film falling freely on a heating wall", Exp. Ht. Transf., V. 4, pp. 217–233, 1991) published an article demonstrating a device that measures the thickness of a wavy film. The invention consists of a wire that penetrates the liquid film and is made of a material that changes resistance with temperature; the instantaneous resistance of the wire is made, from which they are able to predict thickness and temperature profile instantaneously. All of these inventions require contact and penetration of a device into the wet film. There are at least two methods that do not penetrate the film which are used for some dry coating, and probably can be used with wet coatings (see Cross, "Thickness measurements—what do they mean?", Pltng & Surf. Fnshng, November 1979, pp. 22–28). These measure, respectively, eddy currents and magnetic attraction to calculate film thickness. The method claimed herein is non-penetrating and uses an electric field instead and measures the resulting displacement of the free surface from which wet film thickness can be calculated.

A problem with many of the above references is that they do not teach the measurement of viscosity of different layers in a coating traveling on a moving web.

Dynamic viscosity of a liquid and dynamic surface tension of a free surface or interface between a liquid and a gas are concepts that are familiar to most knowledgeable practitioners in the area of fluid mechanics and will not be discussed here. (For brevity, the modifier "dynamic" will be dropped when referring to both properties.) On the other hand, the surface dilational elasticity is not as well known and will be discussed here. (A good textbook in this field is the one edited by E. H. Lucassen-Reynders: "Anionic Surfactants: Physical Chemistry of Surfactant Action", Surfactant Science Series, Vol. 11, Marcel Dekker, Inc., 1981.) Surface dilational elasticity is a measure of the free surface's opposition to being deformed in its own plane (by stretching and compressing). Pure liquids such as pure water do not oppose stretching or compressing so their surface dilational elasticity is zero; however, small amounts of contaminants in the liquid such as dirt or surfactants (including soap) tend to migrate to the free surface and build up the necessary stresses to oppose the motion in some degree. In industrial processes, an interface that possesses this property is frequently useful because waves that would otherwise develop at such a free surface can be damped or even eliminated, providing greater control or uniformity. For liquid films that are coated, such as those found in the painting and coating industry, the free surface's ability to move (or oppose motion) can have a large influence on the flow of the entire liquid film as the ratio of the free surface to liquid volume is so high. Thus the finished quality of the painted or coated film can depend greatly on this property. The importance of the stresses induced at free surfaces is well recognized in the industry. (See, for instance, "Static and dynamic surface tension of aqueous mixtures of surfactants and colloidal lattices", a presentation by I-M. Tricot at the 7th International Coating Process Science and Technology Symposium held in Atlanta, Ga. on Apr. 17–21, 1994.)

Surface dilational elasticity is not an intrinsic property of material in the way that viscosity and static surface tension are, but a manifestation of how various physical processes combine to resist or oppose flow at the free surface. It is defined as the rate of change of the surface tension with respect to the rate of change of the natural logarithm of the surfactant's surface concentration. The principal properties involved are the build-up of surface tension gradients when the surfactant concentration at the free surface varies, and the ability of the surfactant to reach the free surface (by diffusion or convection) from the bulk of the liquid and the rate of distortion of the free surface. However, as the interaction between these properties is very complicated, it is usually more convenient to measure surface dilational elasticity directly.

There are a number of methods of measuring surface dilational elasticity in pools of liquid or for liquids flowing down inclined planes. These methods depend on exciting waves in the film and measuring the degree to which they damp. Some of these methods are described in the aforementioned book by Lucassen-Reynders. They typically rely on producing waves through an oscillatory excitation, including electrostatic excitations by a method called electrocapillarity. (See C. H. Sohl, K. Miyano and J. B. Ketterson, "Novel technique for dynamic surface tension and viscosity measurements at liquid-gas interfaces", Rev. Sci. Instrum., V. 49, p. 1669, 1978.) Although the excitation is similar to the one of the present invention, this other method excites a stationary pool of liquid with a sinusoidal excitation in time. Electrocapillarity has also been used before to excite waves in liquids flowing down an inclined plane (see S. J. Weinstein, J. M. Baumlin and J. Servant, "The propagation of surface waves in flow down an oscillating inclined plane", AIChE Journal, V. 39, pp. 1113–1123, 1993), but the purpose there was simply to measure growth of waves of uncontaminated liquids, and not to measure physical properties, and the excitation was oscillatory. In contrast, the method used here applies a steady electrostatic field that is spatially non-uniform to a liquid film, and relies on the dynamics of that film (which are different from those of a liquid pool or of flow down an inclined plane) to determine the viscosity, surface tension and surface dilational elasticity of the liquid film, which is either stationary or moving at a constant speed under the electrodes used to impose the field.

Steady state spatially non-uniform electrostatic fields create non-uniform normal stresses at the free surface which tend to pull the liquid. Because the pulling action is not uniform, the liquid tends to flow in the direction where the field is strongest and accumulates in this region. This approach has been used to change the thickness of liquid films flowing down a wall, but it is usually applied to enhance condensation of the liquid. For instance, Joos and Snaddon ("Electrostatically enhanced film condensation", J. of Fluid Mechanics, V. 156, pp 23–38, 1985) created such an electric field in a condenser tube by inserting asymmetrically a metal rod into the tube and applied high voltage to the rod. However, this type of application is very different as it involves liquid flowing down the inside of a tube, liquid that is not contaminated and so it has no surface dilational elasticity, and its focus is on increasing heat transfer rates, not on measuring material properties.

When a film is placed horizontally on a support under a spatially non-uniform electric field, other forces appear, such as gravity and surface tension, which tend to oppose this accumulation of liquid. Forces due to viscosity resist the motion, and eventual surface tension gradients (equal to the product of the surface dilational elasticity and the surfactant surface concentration gradient) build up sufficiently to oppose the flow. It is by trying to find relatively simple ways in which these forces interact that is applied in this invention to measure viscosity, surface tension and surface dilational elasticity.

SUMMARY OF THE INVENTION

In accordance with one aspect of the present invention, an apparatus is provided for measuring properties of a liquid film, including viscosity, surface tension and surface dilational elasticity comprising:

a transparent moving support having a liquid on a topside of the support, the liquid having a free surface;

a transparent electrically grounded plate positioned immediately below the support;

a light source positioned below the plate for illuminating the liquid on the support;

an electrostatic leveler positioned above the liquid including:
  a plurality of spaced apart wires extending in a direction parallel to the movement of the support; and a high voltage power supply coupled to the plurality of spaced apart wires wherein when the high voltage is applied to the wires, the free surface of the liquid is distorted;

a device that measures changes in coating thickness free surface position such as a CCD camera positioned above the coating for generating a signal corresponding to the distortion in the free surface of the liquid; and means for processing the signal to determine the properties of the liquid.

In another aspect, the present invention relates to a method for determining viscosity of a liquid comprising:

moving a transparent support at a speed, s, having a liquid on the topside of the support, the liquid having a free surface and a thickness, d;

positioning an electrostatic leveler above the free surface of the liquid which includes:
  a plurality of spaced apart wires extending in a direction parallel to the movement of the support;
  applying a voltage to the spaced apart wires which produces spatially non-uniform electric field $E_f$, with the amplitude of the variation of the square of the electric field at the free surface represented by $\Delta(E_f^2)$, thereby creating a disturbance having an amplitude $\Delta\delta_{FS}$ in the free surface of the liquid film at a distance Z from the location where the liquid film is first exposed to the wires, measured in the direction of motion of the support;

determining the viscosity, μ, of the liquid when the distance Z is very short according to the equation:

$$\mu = \frac{d^3 \epsilon_0 Z}{6s\Delta\delta_{FS}} \left(\frac{2\pi}{\lambda}\right)^2 \Delta(E_f^2)$$

wherein $\epsilon_0$ is the dielectric constant of air; and

λ is the wavelength of the disturbance in a direction perpendicular to the movement of the support at the distance Z.

Units of the parameters in all equations in this patent application belong to a consistent set of units according to the International System of units (SI). Therefore μ is in kg/(ms), s is in m/s, $\epsilon_0$ is in F/m, $\Delta(E_f^2)$ is in V²/m², and d, Z and λ are in m.

In still another aspect, the present invention relates to a method for determining surface tension of a liquid comprising:

moving a transparent support at a speed, s, having a liquid on the topside of the support, the liquid having a free surface and a thickness, d;

positioning an electrostatic leveler above the free surface of the liquid which includes:

a plurality of spaced apart wires extending in a direction parallel to the movement of the support;

applying a voltage to the spaced apart wires which produces spatially nonuniform electric field $E_f$ with the amplitude of the variation of the square of the electric field at the free surface represented by $\Delta(E_f^2)$ thereby creating a disturbance having an amplitude $\Delta\delta_{FS\infty}$ sufficiently far from where the coating is first subjected to the field so that said disturbance is no longer growing;

determining the surface tension σ of the liquid according to the equation:

$$\sigma = \left(\frac{\lambda}{2\pi}\right)^2 \left(\frac{\epsilon_0 \Delta(E_f^2)}{2\Delta\delta_{FS\infty}} - \rho g\right)$$

wherein $\epsilon_0$ is the dielectric constant of air;

ρ is the density of the liquid;

λ is the wavelength of the disturbance which coincides with the separation of the wires, these wires being aligned with the direction of motion of the support, and σ is the surface tension, with units of kg/s².

In still another aspect, the present invention relates to a method for determining the surface dilational elasticity of the free surface, comprising:

moving a transparent support at speed, s, having a liquid on the topside of the support, the liquid having a free surface and a thickness, d;

positioning an electrostatic leveler above the free surface of the liquid which includes:

a plurality of spaced apart wires extending in a direction parallel to the movement of the support;

applying a voltage to the spaced apart wires which produces a spatially non-uniform electric field $E_f$, with the amplitude of the variation of the square of the electric field represented by $\Delta(E_f^2)$, thereby creating a disturbance having an amplitude $\Delta\delta_{FS}$ in the free surface at a distance Z from where the liquid is first exposed to the wires measured in the direction of motion of the support;

determining the surface dilational elasticity by fitting the amplitude of the free surface disturbance $\Delta\delta_{FS}$ as it changes with distance to the following set of equations which contain the surface dilational elasticity e as the only unknown parameter:

$$\Delta\delta_{FS} = \tag{1a}$$

$$\frac{\Delta\delta_{FS\infty}}{2} \left[ \left(1 - \frac{1+3E}{D_{disc}}\right) e^{-\kappa_1 \tau} + \left(1 + \frac{1+3E}{D_{disc}}\right) e^{-\kappa_2 \tau} - 2 \right]$$

wherein $$D_{disc} = \sqrt{(1+3E)^2 - 9E} \tag{1b}$$

$$\kappa_1 = \frac{-3E + 1 - D_{disc}}{6} \tag{1c}$$

$$\kappa_2 = \frac{-3E + 1 + D_{disc}}{6} \tag{1d}$$

$$E = \frac{e}{d^2} \frac{1}{\left[\rho g + \sigma\left(\frac{2\pi}{\lambda}\right)^2\right]} \tag{1e}$$

$$\tau = \frac{d^3}{\mu s} \left(\frac{2\pi}{\lambda}\right)^2 \left[\rho g + \sigma\left(\frac{2\pi}{\lambda}\right)^2\right] Z \tag{1f}$$

and e=2.718282 . . . is the base of the exponential function;

$\Delta\delta_{FS}$ and $\Delta\delta_{FS\infty}$ are, respectively, the displacement of the free surface at each position Z and sufficiently far from where the coating is initially subjected to the electrostatic field so that the disturbance no longer changes;

ρ, μ and σ are, respectively, the density and viscosity of the liquid and the surface tension at the free surface between the liquid and the air;

g is the gravitational constant;

λ is the wavelength of the disturbance which coincides with the separation of the wires, these wires being aligned with the direction of motion of the moving support; and e is the surface dilational elasticity, which is a negative number with units of kg/s² in the SI system of units, and is the only free parameter in the above set of equations.

DETAILED DESCRIPTION OF THE INVENTION

Figure 1:
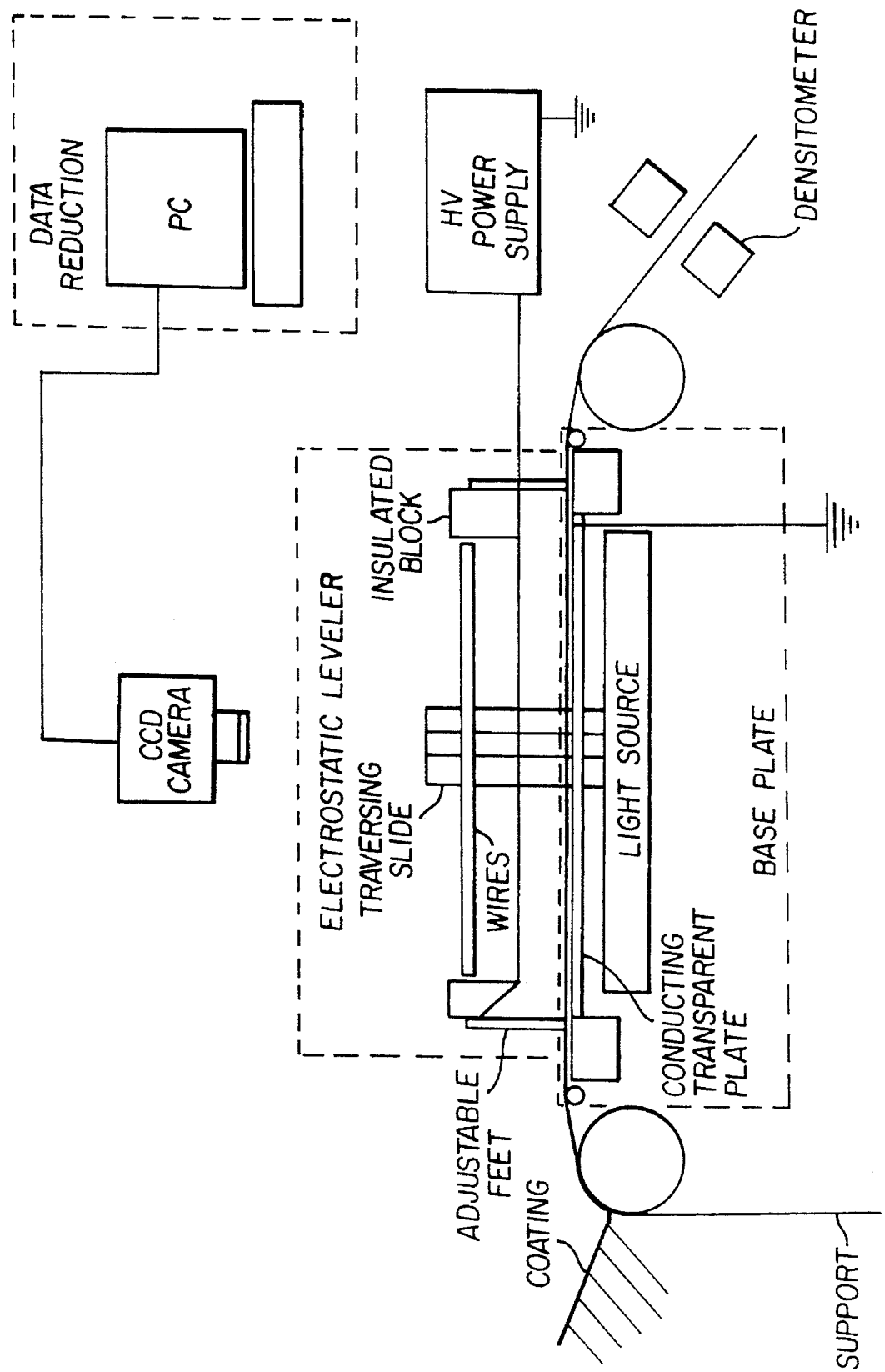
FIG. 1 shows a schematic diagram illustrating the preferred embodiment of the present invention.

The present invention provides an apparatus and a method for the quantitative evaluation of viscosity, surface tension and surface dilational elasticity of a wet coating on a support. The use of the present invention is especially directed to the coating field where moving supports with wet coatings are common. However, with slight modifications, this method can be used for liquid films that are not in motion.

The method is based on a theoretical model described in the paper by Joos, "Leveling of a film with stratified viscosity and insoluble surfactant", in the March 1996 issue of the AIChE Journal and which studies how a liquid levels after it has been uniformly spread on a support that is uneven and resting in a horizontal plane. The liquid is assumed to be contaminated with traces of an insoluble surfactant, which is a good approximation in many coating processes as the rates of change of the flow are usually faster than the rate at which significant amounts of surfactant can be dissolved into the bulk of the liquid. Although it is not immediately apparent, this physical situation is analogous to that of a wet coating lying on a flat horizontal surface that is subjected to a spatially nonuniform electric field at its free surface. In particular, the evolution of the disturbance in film thickness is the same in both situations with the spatially non-uniform electric field playing the role of the wavy unevenness in the uneven support. This critical point is explained later on.

In the theoretical model, a coating is initially applied to (or coated on) a support with uniform coating thickness. Its free surface will adopt the shape of the solid surface below it. Consequently, if the base is uneven, the free surface will neither be level nor flat, and gravitational and capillary forces will induce the film to flow. Its evolution can be described as a series of stages: initial, transitional, and final.

The first stage evolves as if there is no surfactant on the surface of the coating and the leveling is driven by surface tension and gravity alone, and resisted by viscous forces. The film flows from the ridges into the valleys of the support. This is the stage in which the flow is most rapid.

As the initial stage flow progresses, the surfactant concentration becomes less uniform and a surface tension gradient develops on the free surface. In the transitional stage, this gradient causes the free surface to start restoring itself to its original shape and to slow down the flow. In the final stage, the free surface has returned to its original position and the flow is significantly reduced and eventually stops, when the free surface is leveled and there no longer are surface tension (or surfactant surface concentration) gradients.

In the theoretical model the amplitude of the disturbance $\Delta\delta$ in the thickness of a film of uniform dynamic viscosity $\mu$, which rests on a support containing a sinusoidal waviness of wavelength $\lambda$ and amplitude $-\Delta\delta_\infty$, varies with time $t$, according to the following equations:

$$\Delta\delta = \frac{\Delta\delta_\infty}{2}\left[2-\left(1-\frac{1+3E}{D_{disc}}\right)e^{-\kappa_1\tau}-\left(1+\frac{1+3E}{D_{disc}}\right)e^{-\kappa_2\tau}\right] \quad (2a)$$

wherein $$D_{disc} = \sqrt{(1+3E)^2 - 9E} \quad (2b)$$

$$\kappa_1 = \frac{-3E+1-D_{disc}}{6} \quad (2c)$$

$$\kappa_2 = \frac{-3E+1+D_{disc}}{6} \quad (2d)$$

-continued $$E = \frac{e}{d^2}\frac{1}{\left[\rho g + \sigma\left(\frac{2\pi}{\lambda}\right)^2\right]^2} \quad (2e)$$

$$\tau = \frac{d^3}{\mu}\left(\frac{2\pi}{\lambda}\right)^2\left[\rho g + \sigma\left(\frac{2\pi}{\lambda}\right)^2\right]^2 t \quad (2f)$$

and $e=2.718282\ldots$ is the base of the exponential function;

$\sigma$, $\mu$ and $\rho$ are, respectively, the density and viscosity of the liquid and the surface tension at the free surface between the liquid and the air;

g is the gravitational constant;

e is the surface dilational elasticity, which is a negative number.

Although the above relation for film thickness $\Delta\delta$ appears as excessively complicated, it simplifies significantly at the limits of small time (i.e., immediately after the uniform coating started to flow) and after very long times. These represent the initial and final stages, respectively, and the limiting relations are:

$$\Delta\delta \to \frac{\Delta\delta_\infty\tau}{3} = \frac{\Delta\delta_\infty}{3}\frac{d^3}{\mu}\left(\frac{2\pi}{\lambda}\right)^2\left[\rho g + \sigma\left(\frac{2\pi}{\lambda}\right)^2\right]^2 t \text{ as } t\to 0 \quad (3a)$$

and $$\Delta\delta \to \Delta\delta_\infty(1-e^{-\tau/12}) = \quad (3b)$$

$$\Delta\delta_\infty\left(1-\exp\left\{-\frac{d^3}{12\mu}\left(\frac{2\pi}{\lambda}\right)^2\left[\rho g + \sigma\left(\frac{2\pi}{\lambda}\right)^2\right]^2 t\right\}\right) \text{ as } t\to\infty$$

It is to be noted that as time becomes very large the amplitude of the disturbance of the film's thickness is equal to the negative of the amplitude of the support's waviness ($\Delta\delta \to \Delta\delta_\infty$). This simply means that the free surface has flattened so that all the irregularity in the support has been transmitted to the film as a change in thickness. Also to be noticed is that in both these limits the amplitude of the film's thickness is independent of the surface dilational elasticity e.

When a coating lies on a flat support held horizontally, and its free surface is subjected to a sinusoidally varying electric field, normal stresses are developed at that free surface which are analogous to the capillary and gravitational forces in the theoretical problem that are induced initially at the free surface when it is made wavy by the uneven support. In fact, to balance the electrical stresses, viscous forces are established initially, and later liquid accumulates in areas where the field is strongest until the surface tension and gravitational forces become dominant (because of the free surface's unevenness). Eventually, when the balance between the electrostatic forces, and capillary and gravitational forces is complete, the liquid reaches a state of rest with viscous forces and surface tension gradients having become negligible and the free surface taking a wavy shape. The state of rest induced by the so-called electrostatic leveler is that of establishing a wavy interface. The above explains the critical analogy intuitively, and also the reason surface tension and capillary forces are negligible compared to the viscous forces initially, and why viscous forces are negligible compared to capillary and gravitational forces in the final part of the evolution of the flow.

To take advantage of the analogy, it is necessary to determine the analogue between the electric field strength and the final thickness variation $\Delta\delta_\infty$. It is well known in the field of surface waves that if a sinusoidally variable pressure is being exerted at a free surface and the free surface is stationary, then the amplitude of the displacement of the free surface $\Delta\delta_{FS}$ is related to the amplitude of the pressure variation $\Delta p_{FS}$ by:

$$\Delta p_{FS} = -\left[\rho g + \sigma\left(\frac{2\pi}{\lambda}\right)^2\right]\Delta\delta_{FS} \qquad (4)$$

Furthermore, one can derive (see, for instance, the above mentioned paper by Joos and Snaddon), that the amplitude of variation of pressure is proportional to the amplitude of the variation of the square of the field at the free surface taken on the gaseous side, $\Delta(E_f^2)$ $$\Delta p_{FS} = -\frac{(\epsilon_1 - \epsilon_0)}{2}\frac{\epsilon_o}{\epsilon_1}\Delta(E_f^2) \qquad (5a)$$

where $\epsilon_0$ and $\epsilon_1$ are the dielectric constants of the gas and liquid, respectively. It is often the case that the liquid is conducting, so that eq. (5a) can be reduced as if $\epsilon_1 \to \infty$ to:

$$\Delta p_{FS} = -\frac{\epsilon_o}{2}\Delta(E_f^2) \qquad (5b)$$

The field at the free surface depends on the geometry of the electrodes consisting of the wires and their distance from the liquid film, and the voltage drop $V_0$ between the wires and the liquid film (which is essentially grounded by its proximity to the grounded plate):

$$\Delta(E_f^2) = \left(\frac{V_0}{L}\right)^2 f\left(\frac{\lambda}{L}, \frac{D}{L}\right) \qquad (6)$$

where D and L are the diameter of the wires and the distance of the wires from the liquid, respectively, and f is a functional form dependent on the geometric ratios $\lambda$ $\lambda/L$ and D/L.

Combining eqs. (4–6), the relationship between the final displacement of the free surface and the field is determined:

$$\Delta\delta_{FS\infty} = -\frac{\epsilon_0 f}{2}\left(\frac{V_o}{L}\right)^2 \frac{1}{\left[\rho g + \sigma\left(\frac{2\pi}{\lambda}\right)^2\right]} \qquad (7)$$

The functional f depends on the geometry of the electrodes and not on the voltage itself. Assuming that the film thickness and the disturbance of the free surface are small enough not to disturb the electric field, f will be a constant as long as the electrodes (the electrostatic leveler and the grounded plate) and the position of the support are held fixed relative to each other. Once f is known and $\Delta\delta_{FS\infty}$ has been determined using the film thickness measurement system, then eq. (7) can be used to determine the surface tension of the free surface on the support at the position where the measurement is being made.

It is to be noted that the disturbances in free surface displacement, $\Delta\delta_{FS}$ and $\Delta\delta_{FS\infty}$ are the same as the disturbances in film thickness, $\Delta\delta$ and $\Delta\delta_\infty$, respectively, described in the theoretical model by Joos discussed earlier. Equations (3) and (2) can be re-written as:

$$\Delta\delta_{FS} \to \frac{1}{3}\left[\frac{\epsilon_0 f}{2L^2}\right]\left(\frac{2\pi}{\lambda}\right)^2 \frac{d^3 V_0^2 t}{\mu} \text{ as } t \to 0 \qquad (8a)$$

$$\Delta\delta_{FS} \to \left[\frac{\epsilon_0 f}{2L^2}\right]\frac{V_0^2}{\left\{\rho g + \sigma\left(\frac{2\pi}{\lambda}\right)^2\right\}}\left(1 - \exp\left\{-\frac{d^3}{12\mu}\left(\frac{2\pi}{\lambda}\right)^2\left[\rho g + \sigma\left(\frac{2\pi}{\lambda}\right)^2\right]t\right\}\right) \text{ as } t \to \infty \qquad (8b)$$

$$\Delta\delta_{FS} = \frac{1}{2}\left[\frac{\epsilon_0 f}{2L^2}\right]\frac{V_0^2}{\left\{\rho g + \sigma\left(\frac{2\pi}{\lambda}\right)^2\right\}}\left[2 - \left(1 - \frac{1+3E}{D_{disc}}\right)e^{-\kappa_1\tau} - \left(1 + \frac{1+3E}{D_{disc}}\right)e^{-\kappa_2\tau}\right] \qquad (8c)$$

Because the dielectric constant of air $\epsilon_0$ is essentially constant, the first term in square brackets on the right hand side of these equations is solely dependent on geometry, and so it remains a constant from measurement to measurement, as long as the electrode system is not moved and the support always travels along the same plane relative to the grounded plate. Thus, if this term in square brackets is not known, a measurement of the free surface disturbance amplitude for one coating where at least its viscosity or surface tension (preferably both) is known, then the unknown term in the square brackets can be calculated using the above relationships and applied later to films with unknown properties.

It is to be noted also that the above set of equations is in the time variable t because the frame of reference for the model is that of a stationary coating. When the coating is moving at a speed s, then t can be replaced by the ratio Z/s, where Z represents distance from where the liquid is first subjected to the coating in the direction of movement of the support. (Although we will concentrate on the situation where the support moves with respect to the electrodes and the means of measuring film thickness, the method described later can equally be applied to stationary coatings where time t replaces distance Z as the variable.) Making this replacement in eq. (8a), the surface tension and viscosity can be obtained from eqs. (8) as:

$$\sigma = \left\{\left[\frac{\epsilon_0 f}{2L^2}\right]\frac{V_o^2}{\Delta\delta_{FS\infty}} - \rho g\right\}\left(\frac{\lambda}{2\pi}\right)^2 \qquad (9a)$$

when the disturbance no longer grows ($Z \to \infty$)

$$\mu = \left[\frac{\epsilon_0 f}{2L^2}\right]\frac{V_o^2}{3}\left(\frac{2\pi}{\lambda}\right)^2 \frac{d^3 Z}{s\Delta\delta_{FS}} \text{ when } Z \to 0 \qquad (9b)$$

Surface dilational elasticity is determined by simply searching for the surface dilational elasticity e that best fits the eq. (8c) once t is replaced by Z/s. In fact, if necessary, the evolution equation (8c) can be used to determine all three parameters; but it is most convenient to do them separately when enough of the evolution of the flow can be captured in the measurement of the free surface disturbance. In the examples it is shown how to proceed when the instrument does not quite cover the section where the film reaches equilibrium.

To extract these properties from a film under an electrostatic field, it is essential to couple it with a device that can measure the free surface displacement of the film and then be able to reduce the data in such a way that the amplitude of a sinusoidal component of wavelength $\lambda$ can be extracted and observed how it changes with the distance Z. The measurement instrument typically detects changes in film thickness from light that is transmitted through or reflected by the free surface of the coating. If a light transmission technique is used, the support and the coating itself must be translucent to the light. The reduction between the incident light, reaching the first surface of coating or support that is in the path of the light, and the light transmitted, leaving the last surface of the coating or support that is in the path of the light beam, is quantified by a measure called optical density. Often, the optical density of the coating is provided by some dye or small particle dispersion added to the coating so that, at the wavelength of the incident light, the light-measuring instrument is sensitive to small changes in optical density of the coating due to changes in thickness. No other requirements have to be made regarding the coating material except, possibly, those of safety; however, if the liquid and gas combination may explode in the presence of electrical sparks. (The reflected light method described in the paper by Sohl, Miyano and Ketterson, (Rev. Sci. Instrum., Vol. 49(10) October 1978, pp. 1464–1469 can be adapted—with some work—to the present setup, and should be favored when it is undesirable or not possible to transmit light through the coating or its support.)

DETAILED DESCRIPTION OF THE PREFERRED EMBODIMENT AND METHOD

An apparatus and method have been devised by the inventors that can simulate electrostatic leveling repeatedly from which detailed quantitative measurements can be made. The device consists of a series of wires that is placed above the moving wet coating to which a high voltage is applied. The voltage induces an electrostatic force field that exactly simulates the effect of an uneven support. An image of the coating is taken with a CCD camera as the motion of the coated film evolves under the wires. The data from the image is reduced to a curve of lengthwise coating thickness non-uniformity.

The present invention accordingly describes a controlled excitation of the flow produced by an electrostatic field applied directly above the coating on a web. FIG. 1 shows a schematic diagram illustrating the experimental arrangement used to produce the evolution of the flow which is installed on a coating machine that allows access to the coating after the application of the solution. In FIG. 1 there are several different parts to the apparatus, shown blocked off, which are described separately in the following paragraphs.

Base Plate. The grounded base plate over which the web travels is made of a conducting metal frame with a small roller located at each end. Inside the frame there is a viewing window which is 0.10 m wide and 0.23 m long. The glass plate is coated with a transparent conductive film of tin oxide, electrically connected to the frame, which is itself grounded electrically. The coated web travels slightly above the grounded plate, guided by the rollers installed at both ends of the metallic frame. A large flat bed light source (at least as large as the viewing window) is placed under the entire assembly to provide transmitted light through the coating.

Figure 2:
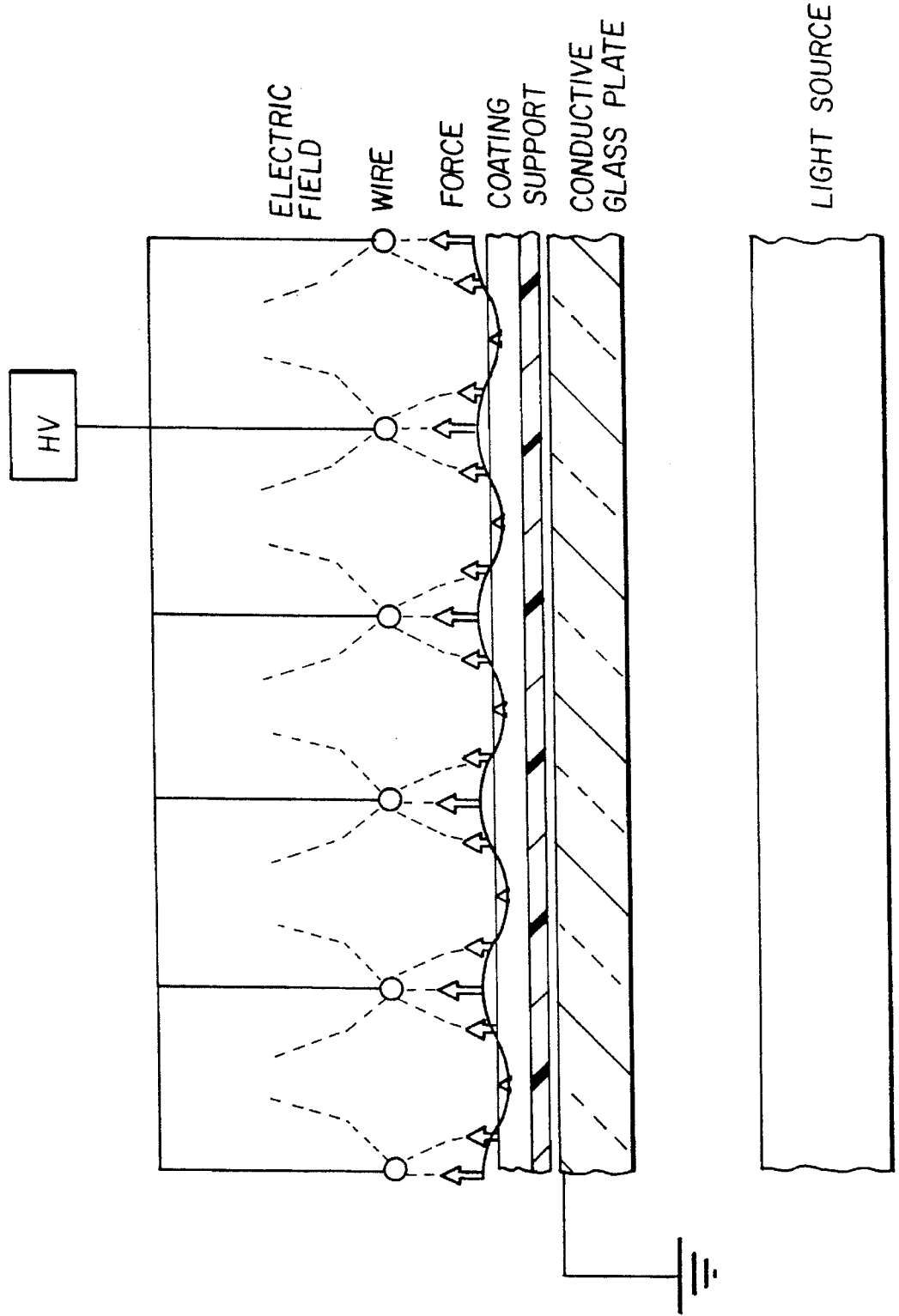
FIG. 2 shows a cross section of the electrostatic leveler shown in FIG. 1.

Electrostatic Leveler. The electrostatic leveler is installed above the support, as shown in FIG. 1 and more clearly, in FIG. 2, where it is given in cross-section. This device is used to maintain a steady electrostatic field over the coating, uniform in the direction of motion of the support but periodic in the perpendicular direction. The field is established by fifteen parallel piano wires, spaced 7 mm apart (so $\lambda=7$ mm), tensioned on another lightweight rigid frame and supported by four adjustable feet that fit in the holes on the base plate. Typically the wires are held 3 mm from the surface of the coating (so $L=3$ mm), which is about half the wire spacing. The diameter of the wires is about 1 mm (so $D=1$ mm), which is smaller but comparable in size to the separation between the wires and coating. It is critical that the wires on this device be kept parallel to the support, and that no conducting part on it be closer to the coating than the wires.

To achieve the parallelism between the grounded base plate and the wires, and to establish the desired spacing between them, a traversing slide with a vernier read-out is mounted to the frame of the grounded plate and attached, with adjustable set screws, to the electrostatic leveler's frame. Before installing the apparatus on a coating machine, the assembly is placed on a massive, flat and leveled granite stone table that ensures that the base plate is leveled throughout the procedure described in this paragraph. Then the frame of the electrostatic leveler is lowered so that the wire electrodes are in contact with the upper surface of the grounded plate, and the set screws connecting the leveler's frame to the traversing slide are tightened. The frame is then raised vertically away from the grounded plate by allowing the traversing unit to slide. The distance L between the grounded plate and the wires is fixed by using the vernier readout on the traversing slide that measures the distance traversed, and then the traverse is locked in position. To ensure that the electrostatic leveler remains parallel to the grounded plate, a level is placed at several positions on its frame and then the frame's feet that rest on the grounded plate assembly are adjusted to fix the relative distances between the wires and grounded plate. The conductive path between the high voltage wires and the frame of the electrostatic leveler is broken by the non conducting polycarbonate blocks mounted to the ends of the frame and the wires are attached to these blocks.

Power Supply. A high voltage power supply is connected to the leveler to produce the electric field. Typically, the voltage applied to the wires is between 1 and 3 kV (so $V_0=1$ to 3 kV). The base plate is connected to a common ground with the high voltage power supply, so the full voltage drop is virtually achieved between the wires and the coated surface. In this configuration, sparking between the wires and the coating (corona discharge) typically occurs above 5 KV.

CCD Camera. A black dispersion is used to supply a neutral optical density to the coatings and the material for the support is essentially transparent. Optical density variations on the coating are then measured using a CCD camera of sufficiently high resolution and a densitometer installed nearby in the path of the coated support to establish the relationship between film thickness and optical density. The following procedure is used to acquire and store the data.

o The size of the image captured is arranged to include the coating that is perturbed by the electric field and omits the peripheral area not associated with the coating.

o The images that are captured must undergo a "flat-field correction", and can be enhanced and compressed if necessary, and stored on a PC hard drive and then transferred to a computer that will process the data.

Figure 3:
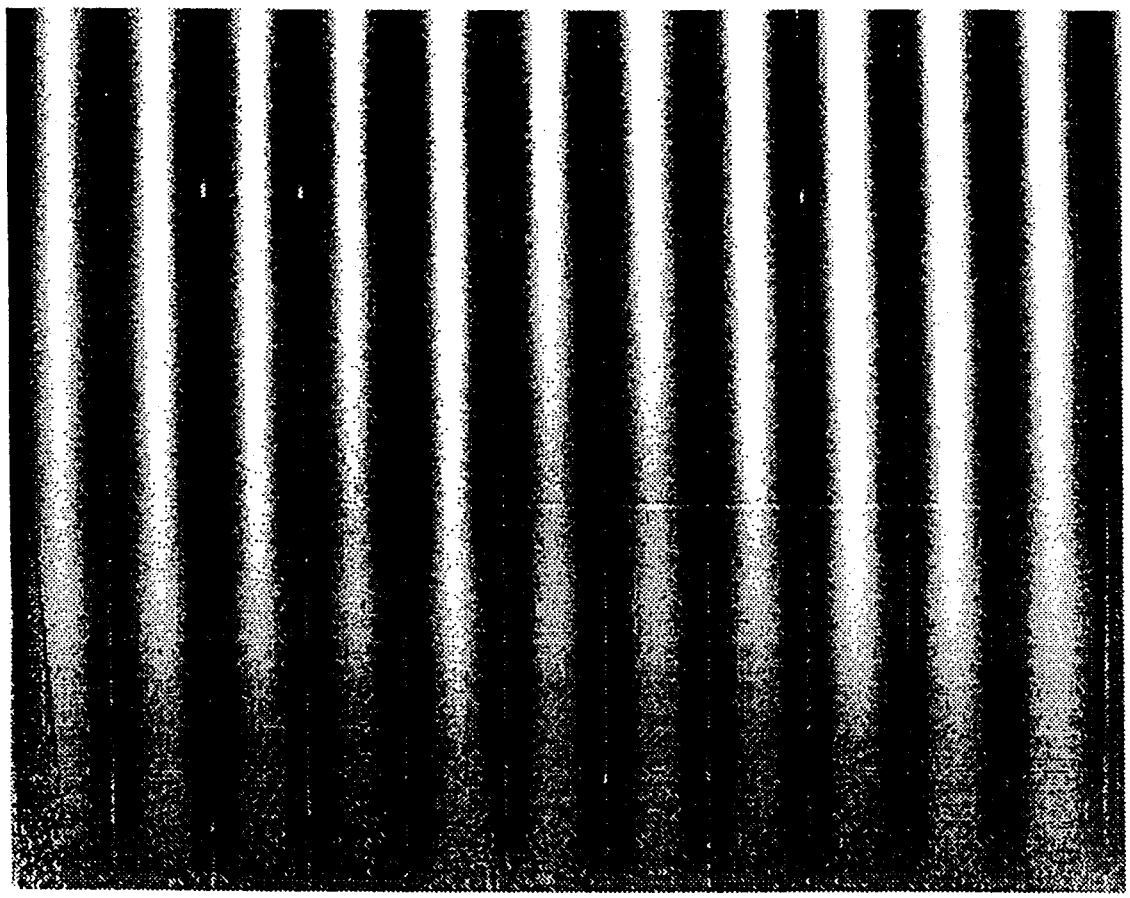
FIG. 3 shows a "flat-field corrected", reduced image with enhanced contrast obtained using the CCD camera.

FIG. 3 shows a typical "flat-field corrected", reduced image with enhanced contrast. The coating direction is from bottom to top and a faint image of the wires can be seen as narrow, light, vertical lines within the dark bands. In the darker regions of the image where the electric field is stronger, the surface is attracted by the wires producing higher optical density (thicker coatings). It is evident in FIG. 3 that there is no deformation initially (bottom side of image) where the coating enters the viewing window. The perturbation becomes greater with time and increases at a decreasing rate as the coating moves to the other end (top side) of the test section.

Figure 4:
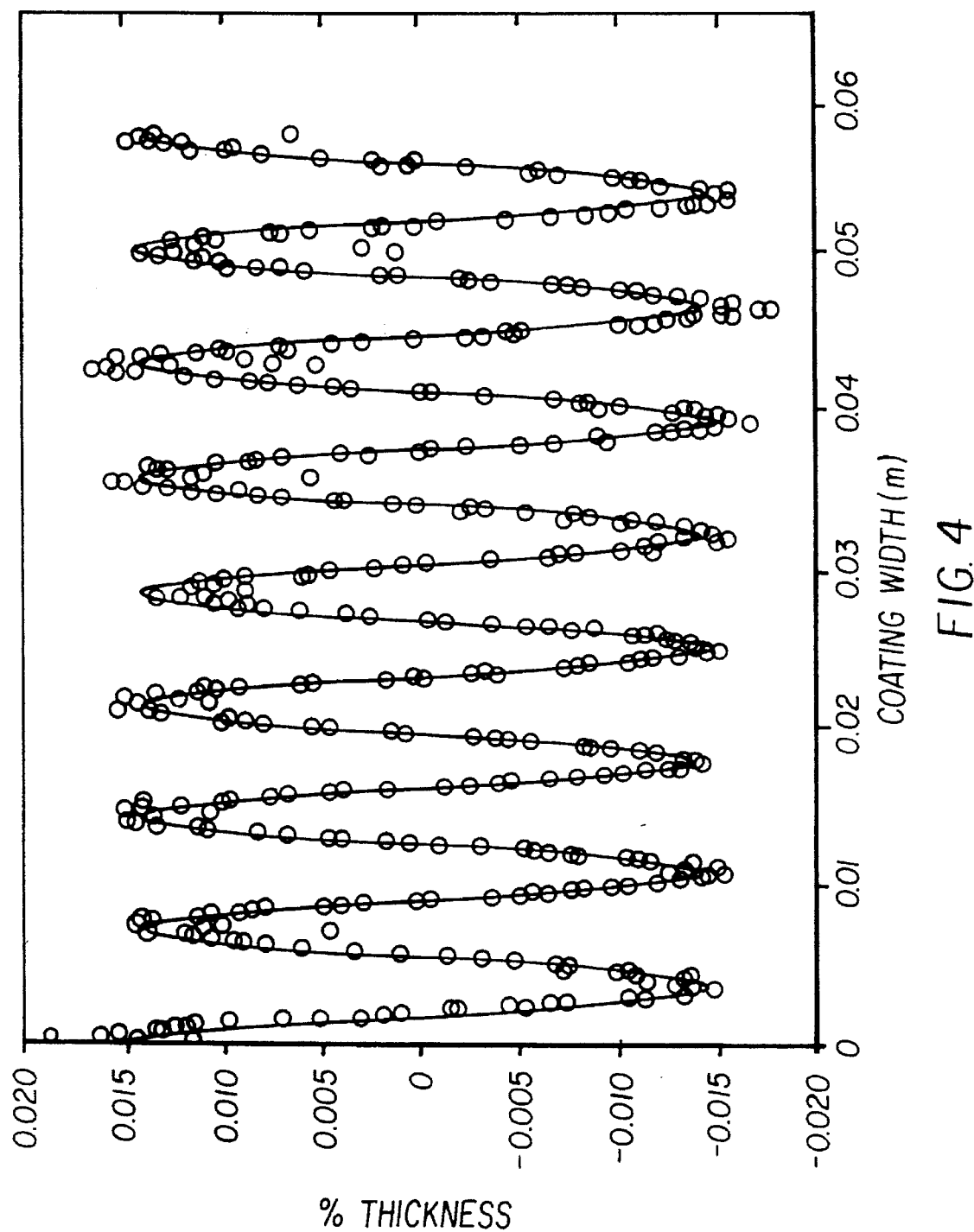
FIG. 4 shows a cross section of coating thickness and its sinusoidal fit of wavelength λ, equal to the spacing between the wires.

Data Reduction. The evolution of the non-uniformity in the coating is obtained by further analysis of the data using a software package on a computer. Each column of the digital image file, which represents a cross-section of the non-uniformity in the widthwise direction, is reduced to a single number, the amplitude of a sinusoidal wave of period equal to the wire spacing that best fits the data. The success of the approach is demonstrated in the comparison of the sinusoidal fit with raw data from a column that is shown in FIG. 4, corresponding to a cross section near the top end of the digital image represented in FIG. 3.

The full evolution of the flow can be obtained by calculating the amplitude of the sinusoidal cross section profile sequentially for each of the image's columns. The amplitude $\Delta\delta_{FS}$ of the sine wave is plotted against time t or distance Z. In FIGS. 5–8, the amplitude is represented as amplitude of the disturbance in μm.

Figure 5:
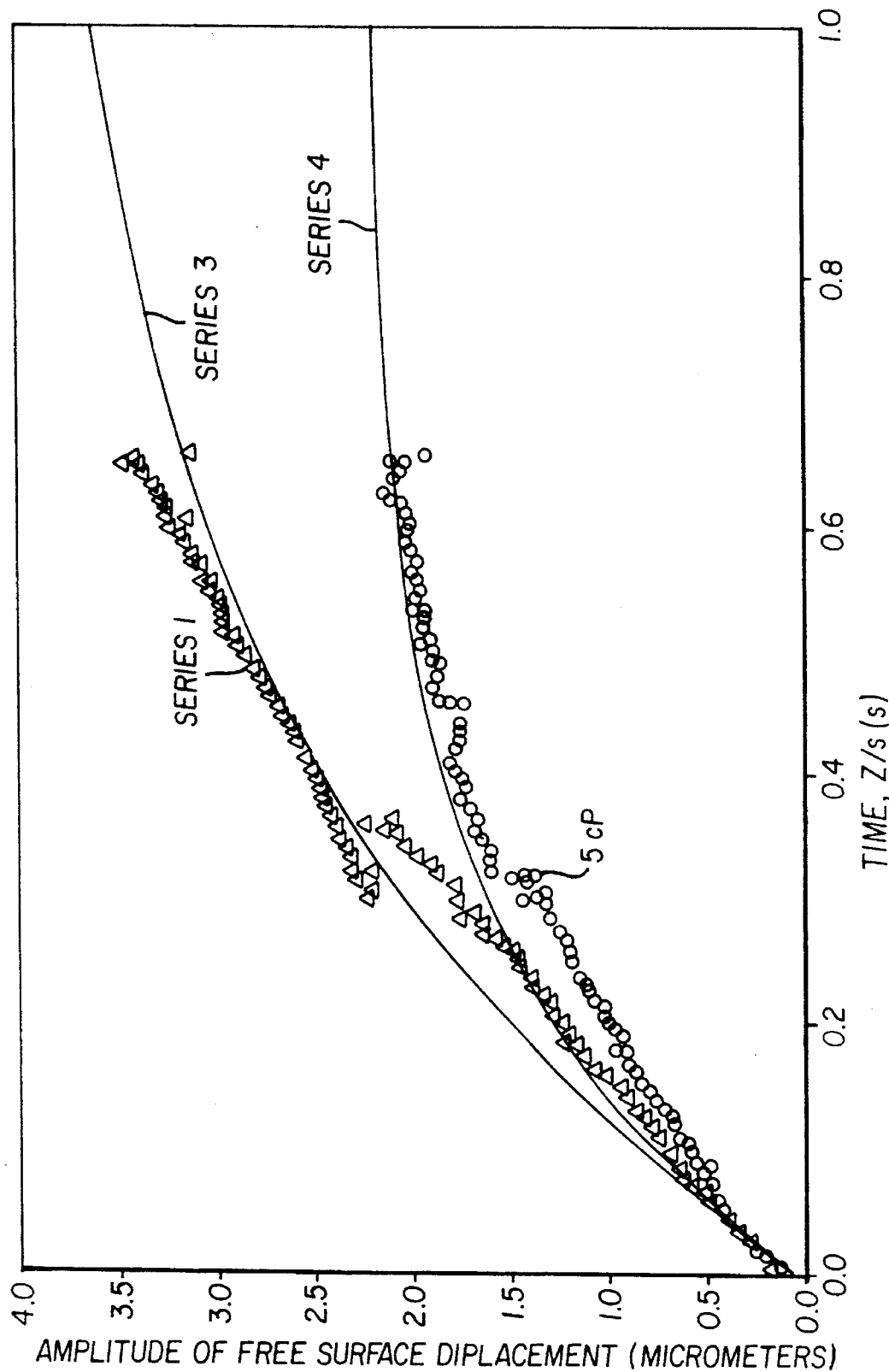
FIG. 5 shows the application of the apparatus and method to measuring surface tension.
Figure 6:
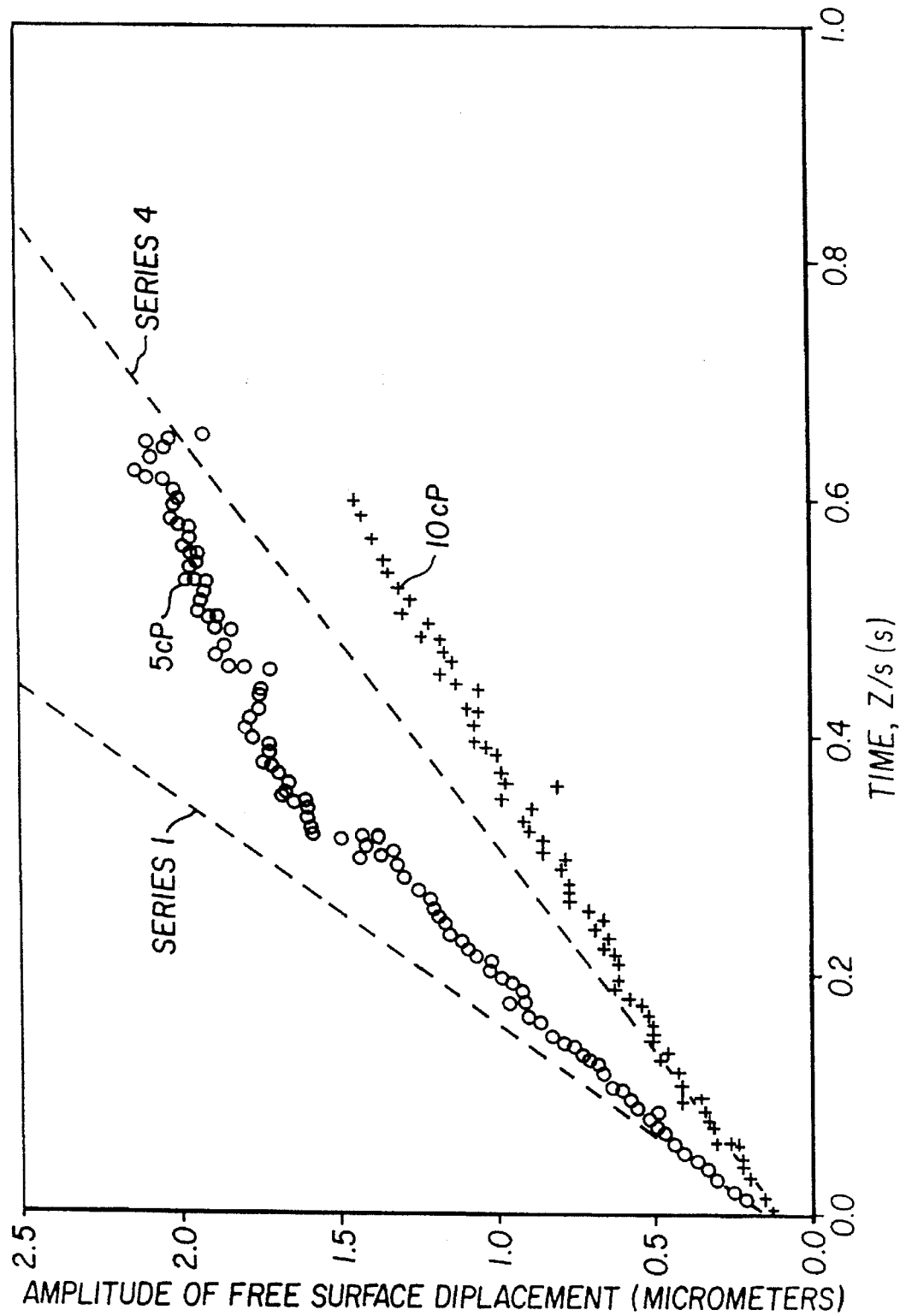
FIG. 6 shows the application of the apparatus and method to measuring viscosity.
Figure 7:
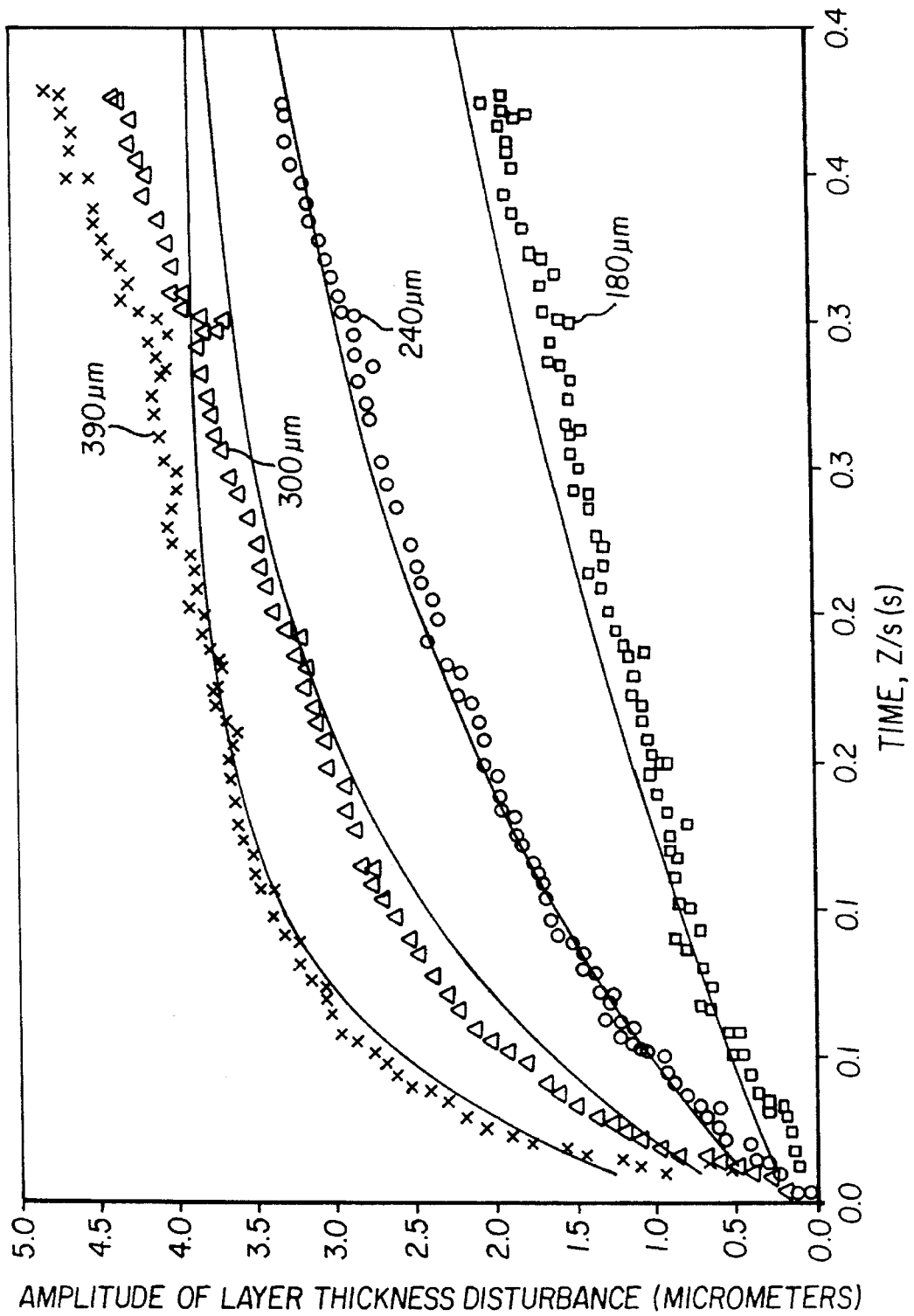
FIG. 7 shows the application of the apparatus and method to measuring surface dilational elasticity.

FIGS. 5 to 7 illustrate the results one obtains, where the experimental data points for different experimental conditions is given by the circles. A direct comparison between theory and experiment is not possible as the actual amplitude of the sinusoidal component for the electrostatic force per unit area at the coating's free surface is not known because the factor of proportionality f(λ/L, D/L) has not been calculated. This factor depends strictly on the geometry of the high voltage electrode and its spacing from the coating. As a form of calibration, the data for one experimental condition (the check or standard condition) is used to fit the undetermined parameter, and then the other experimental data is compared directly with the predictions. In a more precise setup, it would be possible to calculate the factor f(λ/L, D/L).

1) The calibration constant, $A=(\epsilon_0 f V_0)/(2L^2)$, is determined by one or two methods for the check or standard condition:

o The slope of the amplitude of the free surface disturbance $\Delta\delta_{FS}$ as it changes with distance Z is determined at the inlet end of the test section with respect to distance divided by coating speed, Z/s. The thickness d of the coating is established by controlling the flow per unit width of the coated support and the speed at which the support travels. As the viscosity μ is known for the standard condition, eq. (9b) can be used to find the unknown calibration constant. (If the voltage $V_0$ is to be changed during an experiment, then of course it is left out of the calibration constant A and kept as a separate parameter.)

o If enough of the evolution of the free surface disturbance has been obtained in the image so that it has become constant with time for the standard condition, the calibration constant A can also be calculated using eq. (9a) instead. It is assumed here that the liquid density σ is known fairly well through other means, as is usually the case.

When both methods are available, an average of the two estimates can be used for the measurements of viscosity, surface tension and surface dilational elasticity for the coatings where these properties are unknown.

2) Holding constant the spacing between the electrodes, the support and the grounded plate, and also possibly the voltage of the electrodes, the evolution of the amplitude of the free surface's disturbance for the coating samples to be measured is determined as mentioned earlier. The other parameters such as coating thickness and density are determined independently.

o The viscosity is found from the slope of the curve at the inlet point (Z=0) using eq. (9b) where the term in square brackets is replaced by the calibration constant A.

o If the measurement of surface disturbance covers the end of the evolution where it becomes constant, then eq. (9a) can be used to calculate the surface tension ρ once the term in square brackets is replaced by 3A. If the evolution has not proceeded to completion, then it is often the case that the last part of the measurement obtained is in the final stage discussed earlier and its last segment can be fit by eq. (8b), where the surface tension ρ is the unknown variable and t is replaced by Z/s as discussed earlier. Otherwise, this measurement would require lengthening the test section, or reducing the coating speed, or reducing the spacing between the wires.

o Lastly, the surface dilational elasticity e is determined (together with the surface tension ρ if it was not obtainable by the previous step) by allowing the unknown parameter(s) to vary until eq. (8c) fits the experimental data the best.

Several example applications are presented here, showing how the method can be used to measure surface tension, viscosity and surface elasticity. In the examples, the coatings consist of aqueous solutions of gelatin with a black carbon dispersion. However, the method and apparatus can be used for other liquid films. Table 1 presents the experimental details.

TABLE 1

Experimental Conditions for Data in FIGS. 5 to 8

| Figure | Coating Speed (m/s) | Viscosity (kg/(ms)) | Wet coverage (μm) | Surfactant | Surfactant Conc. (% w/w) | Optical dispersion placement from support (μm) |
|---|---|---|---|---|---|---|
| 5 | 0.25 | 0.005 | 175 | TX200E | 0.01 | Entire coating |
| * | 0.25 | 0.005 | 175 | — | — | Entire coating |
| 6 | 0.15 | 0.010 | 175 | — | — | Entire coating |
| * | 0.25 | 0.005 | 175 | — | — | Entire coating |
| 7 | 0.60 | 0.0114 | 180 | — | — | Entire coating |
| * | 0.60 | 0.0114 | 240 | — | — | Entire coating |
|   | 0.60 | 0.0114 | 300 | — | — | Entire coating |
|   | 0.60 | 0.0114 | 390 | — | — | Entire coating |
| 8 | 0.40 | 0.0114 | 350 | — | — | 25–125 |
| * | 0.40 | 0.0114 | 350 | — | — | 125–225 |
|   | 0.40 | 0.0114 | 350 | — | — | 225–325 |

Notes:
An asterisk in the first column indicates the check condition of the figure.
All experiments presented were performed at 2kV(DC) with distance between the wires and the plate between 2.5 and 3 mm.

EXAMPLE - 1

Surface Tension Measurement

FIG. 5 compares the free surface displacement of two coatings with the same viscosity and thickness, one with and the other without traces of a surfactant mixed in. (It is well known that small concentrations of surfactant can significantly reduce the surface tension of a liquid.) The data points arise from two separate measurements that are, unfortunately, distorted by a "smile" due to a poor flat field correction and for this reason the data points don't lie on smooth curves. The distortion makes comparisons difficult, especially for surface dilational elasticity, for which the entire evolution must be considered, and to a significant extent, surface tension, if the growth has not stopped and the later part of the data must be fit to the final stage prediction, eq. (8b). For this reason, surface dilational elasticity will not be measured in this example. Later measurements do not suffer from this problem.

The trajectory of the two curves starts out the same, which confirms that the viscosities are equal (as the thicknesses d are also the same). As surfactant lowers the surface tension of the free surface significantly, the coating containing surfactant eventually experiences a larger free surface displacement. The data obtained for both coatings excludes the very late stage in which the free surface displacement becomes constant, so the calibration constant A has been obtained by fitting eq. (8b) for the final stage to the second part of the trajectory of the standard or check coating. For an aqueous gelatin solution with a free surface made less than a second earlier at the point where the coating is applied to the support, surface tension can be measured independently at approximately 0.062 kg/s². Applying this value of surface tension and the viscosity given in Table 1, eq. (8b) yields A=0.1326 kg/(ms²). Fitting eq. (8b) to the data of the coating with surfactant using this value of the calibration constant, surface tension is measured at $\rho \equiv 0.029$ kg/s², approximately. This is not too close to an independent reading of 0.034 kg/s² for the surface tension for aqueous gelatin with that surfactant at the same concentration; probably more accurate measurements with this apparatus would be achieved if the flat-field correction had been accurate.

EXAMPLE - 2

Viscosity Measurement

FIG. 6 shows the initial part of the evolution of the amplitude of the free surface displacement, the viscosity of the check or standard coating being of 0.005 kg/(ms) and the other of 0.010 kg/(ms). In eq.(9b), the only two parameters that vary between these two coating conditions are the viscosity $\mu$ and the corresponding amplitude of the free surface disturbance $\Delta\delta_{FS}$. Indeed, the product of viscosity and free surface displacement amplitude, or, for that matter, of viscosity and the initial slope of the displacement, $\Delta\delta_{FS}/(Z/s)$, ought to be constant. The slopes (near the origin) for the lower and higher viscosity coatings are, respectively, 5.30 and 2.88 μm/s; as the ratio of the slopes is equal to the inverse ratio of the respective viscosities, the higher viscosity is calculated and measured as 0.092 kg/(ms), which is fairly good.

EXAMPLE - 3

Surface Dilational Elasticity Measurement

FIG. 7 shows the evolution of the amplitude of the free surface disturbance for four coatings of aqueous gelatin of viscosity 0.0114 kg/(ms), surface tension 0.062 kg/s² and of different thickness. As the coatings consist of the same material and the surface age of the free surfaces are the same at the point of the measurement, it is reasonable to assume that the surface dilational elasticity is the same in all cases. Taking the coating that is 240 μm thick as the check or standard condition, the calibration constant is found using eq. (8b) with the above-mentioned surface tension and viscosity to calculate A=0.2319 kg/(ms²). Equation (8c) is then applied to fit the check or standard condition by varying the surface dilational elasticity parameter (e≡−0.010 kg/s²), and then applying that elasticity parameter to eq. (8c) for the other coatings. The continuous lines are those due to the fit; it is clear that the selected value of the surface dilational elasticity applies fairly well to all coatings.

ALTERNATIVE APPLICATIONS AND METHODS

The apparatus, either in its present or some other embodiment, can be applied to make other measurements, or the same measurements with a slightly different method. The following examples discuss some of these.

EXAMPLE - 4

Film Coating Thickness Measurement

In some processes the film thickness is not directly controlled by the process (such as in self-metering coating processes as roll and dip coating) but is a variable that needs to be measured. It is advantageous to apply eq. (9b) to determine the coating thickness d if the following conditions hold:

- film thickness cannot be obtained directly with light transmission measurements, either because the support or coating is opaque, or because it is undesirable that light penetrate the support, or because the optical density of the support is unknown (perhaps due to previously applied coatings of unknown optical density);
- the viscosity $\mu$ of the film is known; and
- it is possible to determine the amplitude of the displacement of the free surface $\Delta\delta_{FS}$, either by a reflective technique or by transmitting light through the film and knowing the relationship between a change in film thickness and change in optical density.

Then eq. (9b) can be re-written to predict the film thickness d:

$$d = \left\{ \frac{6\mu s \Delta\delta_{FS}/Z}{\epsilon_d V_o^2/L^2} \left(\frac{\lambda}{2\pi}\right)^2 \right\}^{1/3} \quad (10)$$

Table 2 presents an application of this method to the same data discussed in Example 3 and FIG. 7. The slope of the curves (near the origin) at the inlet $\Delta\delta_{FS}(s/Z)$ is extracted from FIG. 8 and inserted in eq. (10) to find the measured thickness, and the agreement is fairly good.

TABLE 2

| Actual Thickness (μm) | Measured Thickness (μm) |
|---|---|
| 180 | 174 |
| 300 | 311 |
| 390 | 396 |

Although this method of measuring film thickness disturbs the coating, it will not leave a streak in a coating, even if it has multiple layers, as long as the coating has enough time to level before setting or drying. Thus, used properly, this method has the advantage of being non-destructive.

EXAMPLE - 5

Surface Dilational Elasticity Measurement From Multiple-Layer Data

Figure 8:
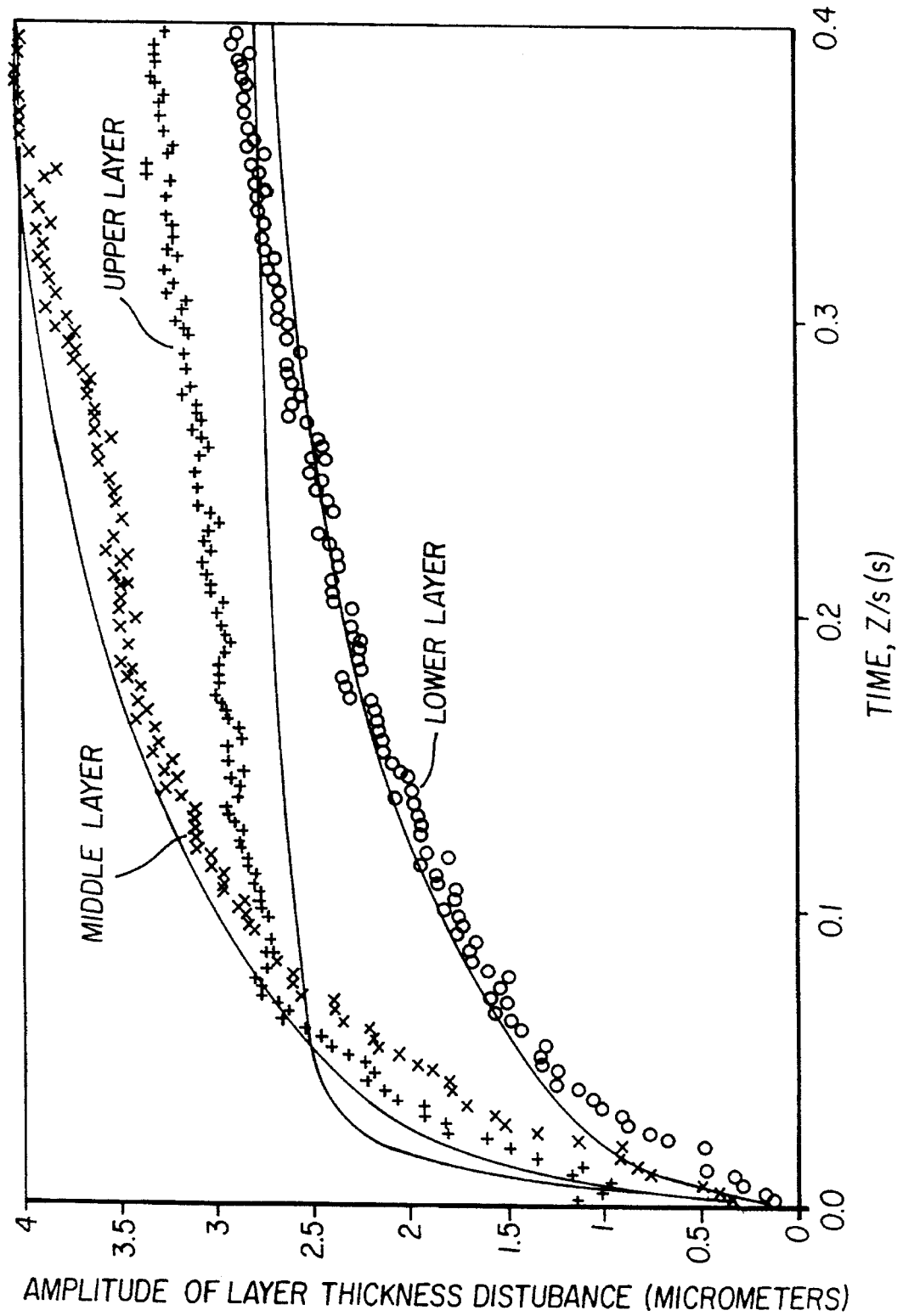
FIG. 8 shows the application of the apparatus and method to measuring surface dilational elasticity from multiple layer data.

FIG. 8 shows the evolution of the amplitude of the thickness variation of three different inner layers of the coating taken with the preferred embodiment of the apparatus. The selected placement of the optical dispersion is achieved by applying the coating to the support as a multiple layer coating (very common in the photographic coating industry) and adding the dispersion to only one layer at a time. The theoretical model from which eqs. (2) originate also predicts the flow of stratified layers of equal or different viscosities. (In this example the coating's viscosity is uniform.) The evolution takes the characteristic shape shown in the figure when a surfactant is present, namely that, initially, the rate of change in thickness increases with the distance of the layer from the support, but eventually the disturbance in the higher layer grows more slowly or even decreases while those of the other layers increase at a relatively greater rate. As the viscosity (0.0114 kg/(ms)) and surface tension (0.062 kg/s$^2$) are known, it is sufficient to find the calibration coefficient A and the surface dilational elasticity e that best fit the appropriate equation for films of multiple layers. The solid curves are for A=0.6024 kg/(ms$^2$) and e=−0.002 kg/s$^2$.

EXAMPLE - 6

Viscosity of Individual Layers and Surface Dilational Elasticity For Coatings of Multiple Layers If the thickness is known for each layer in a coating of n layers of roughly the same density, and if it is possible to measure the thickness variation of each layer independently as the coating is subjected to the electrostatic field, then the viscosity of each individual layer can be measured with this device. In principle, this is accomplished by fitting the curves for the evolution predicted for each layer and the entire coating with the surface elasticity, surface tension and viscosities as variables. The task can be simplified by using the following procedure which is similar to the recipe for films of uniform viscosity:

o Determine the calibration constant A as before from a coating of one layer with known properties.

Establish the viscosities of the different layers from the slope of the amplitude of thickness disturbances of each layer when the electrostatic excitation starts. According to the theoretical model in the above mentioned paper by Joos, eq. (9b) yields an effective viscosity $\mu_{\it eff}$ for the entire film (i.e. $\mu_{\it eff}$ replaces $\mu$ in that equation) and, denoting the amplitude of the thickness disturbance of the i$^{th}$ layer by $\Delta\delta_i$, the viscosity $\mu_i$ of that layer is related to the effective viscosity $\mu_{\it eff}$ and the viscosities $\mu_j$ of the layers below it by:

$$\sum_{j=1}^{i-1} \frac{D_{ij}}{\mu_j} + \frac{1}{\mu_i} \int_{y_{i-1}}^{y_i} \left[ \int_{y_{i-1}}^{y'} (d-y'')dy'' \right] dy' = \frac{\Delta\delta_i}{\Delta\delta_{FS}} \frac{d^3}{3\mu_{\it eff}} \text{ for } i=1,2,\ldots,n \quad (11a)$$

wherein $$D_{ij} = (y_i - y_{i-1}) \int_{y_{j-1}}^{y_j} (d-y')dy'; \quad (11b)$$

and $y_i$ is the upper interface of the i$^{th}$ layer; and $$\sum_{j=1}^{i-1} \frac{D_{ij}}{\mu_j} = 0$$

when i=1, on the left side of Eq.(11a). There are n layers in the coating ordered sequentially from the support to the free surface, with the layer adjacent to the support corresponding to i=1. Equation (11a) makes up a set of n linear equations with n unknowns, the $1/\mu_i$. This linear set of equations can then be solved using conventional matrix inversion techniques.

The surface tension is determined from eq. (9a) as before, as long as the free surface disturbance has stopped growing within the test section. If this is not the case, then eq. (8b) is applied where the film's viscosity $\mu$ is replaced by another effective viscosity $\mu'_{\it eff}$:

$$\frac{1}{\mu'_{\it eff}} = \frac{12}{d^3} \sum_{i=1}^{n} \frac{1}{\mu_i} \int_{y_{i-1}}^{y_i} (y_M - y)^2 dy \quad (12a)$$

wherein $$y_M = \frac{\sum_{i=1}^{n} \frac{(y_i^2 - y_{i-1}^2)}{\mu_i}}{2 \sum_{i=1}^{n} \frac{(y_i - y_{i-1})}{\mu_i}} \quad (12b)$$

o The surface dilational elasticity is determined by determining the best fit to a generalized version of eq. (8c):

$$\Delta\delta_{FS} = \left[ \frac{\epsilon_0 f}{4L^2} \right] \frac{V_0^2}{\left\{ \rho g + \sigma\left(\frac{2\pi}{\lambda}\right) \right\}} \left[ 2 - \left(1 - \frac{I_2 + 3I_0 E}{D_{disc}}\right) e^{-\kappa_1 \tau} - \left(1 + \frac{I_2 + 3I_0 E}{D_{disc}}\right) e^{-\kappa_2 \tau} \right] \quad (13a)$$

wherein $$I_j = \frac{\mu_1}{d^{j+1}} \sum_{i=1}^{n} \frac{(d-y_{i-1})^{j+1} - (d-y_i)^{j+1}}{\mu_i} \text{ for } j=0,1,2 \quad (13b)$$

and the following symbols are redefined:

$$\Delta = \sqrt{(I_2 + 3I_0 E)^2 - 9I_1 E} \quad (13c)$$

$$\kappa_1 = \frac{-3I_0 E + I_2 - D_{disc}}{6} \quad (13d)$$

$$\kappa_2 = \frac{-3I_0 E + I_2 + D_{disc}}{6} \quad (13e)$$

$$\tau = \frac{d^3}{\mu_1} \left(\frac{2\pi}{\lambda}\right)^2 \left[\rho g + \sigma\left(\frac{2\pi}{\lambda}\right)^2\right] t \quad (13f)$$

It is indeed possible to measure thickness variation of individual layers simultaneously using a transmission technique if the different layers are transparent to all wavebands of electromagnetic radiation (visible light, infrared light, ultraviolet light) except for a specific waveband for which it provides optical density, and this specific waveband is different for the different layers. By transmitting simultaneously light that includes radiation in the wavebands that are translucent (i.e. wavebands that provide some transmission loss or optical density) for all the layers, and appropriate filtering of the light that reaches the receiver, the change in optical density (and therefore thickness) of each layer can be determined. For laboratory work, it may be simpler to place the dye or dispersion in each layer on different occasions and pass the coating through the apparatus for separate measurement of the change in thickness of the layer. This is indeed how the measurements in FIG. 8 were performed.

EXAMPLE - 7

Alternative Electrode Designs

The spacing between the wire electrodes of the electrostatic leveler dictates the rate at which the evolution of the disturbance occurs. By changing the distance between the wires, it is possible to change the rate of evolution and thus shorten the length of the device or apply the same device to the same coatings but at higher speeds, or thinner coatings at the same speed. However, as eq. (7) indicates, reducing the wavelength or spacing $\lambda$ has the effect of reducing the final free surface disturbance amplitude $\Delta \delta_{FS}$ if the field (nominally $V_0/L$), and all the geometric aspect ratios are kept constant. Thus reducing spacing between wires may require more sensitive equipment to measure the change in free surface displacement.

If it is desired that the variation of the field at the free surface more closely resemble a more specific wave shape such as a sine wave, it is possible to either optimize the geometry of the assembly by changing the ratios of wavelength to wire-grounded plate spacing $\lambda/L$ and the wire diameter to wire-grounded plate spacing $D/L$, or to reverse the polarity of every second wire, or to add sets of more wires between the present wires and supply these new wires with different intermediate voltages in such a manner that the field at the free surface more closely resembles the desired wave shape.

Although it seems best, it is not necessary for the high voltage electrode to consist of a uniform array of equally spaced wires set in a plane parallel to the support and aligned in the direction of motion of the support. A single electrode such as a conductive rod or strip with the same alignment may be sufficient to extract the coating properties of interest. Furthermore, if only viscosity or thickness of the coating is required, then any shape of electrode will be suitable after the calibration factor has been determined experimentally because, in eq. (9b), a change in viscosity $\mu$ or thickness $d$ affects the free surface displacement by the same proportion, independently of the wavelength $\lambda$ or the geometric factor $f$, which are the terms in the equation affected by variable shape.

EXAMPLE - 8

Time-Dependent Measurements

When performing on-line measurements, the preferred embodiment should be favored as the support is typically in motion. However, with slight changes to the method, the apparatus can be applied when the support is stationary with respect to the coated support. Then the evolution progresses in time and, in the direction of the wires, it will be the same everywhere under the apparatus. To measure the evolution it is necessary to measure the amplitude of the free surface displacement as time progresses. With a CCD camera, this requires taking several consecutive images. The determination of the physical properties of the coating is identical except that now time $t$ (in seconds) replaces the ratio $Z/s$ in eqs. (9). There are no further complications in making this change.

The invention has been described in detail with particular reference to certain preferred embodiments thereof, but it will be understood that variations and modifications can be effected within the spirit and scope of the invention.

What is claimed is:

1. An apparatus for measuring properties of a liquid film, including viscosity, thickness, surface tension and surface dilational elasticity, comprising:
   a transparent moving support having a liquid film or coating on a topside of the support, the liquid having a free surface;
   a transparent grounded plate positioned below the support;
   a means for illuminating the liquid on the support from below the plate;
   an electrostatic leveler positioned above the liquid including:
      a plurality of spaced apart wires extending in a direction parallel to the movement of the support; and a high voltage power supply coupled to the plurality of spaced apart wires wherein when the high voltage is applied to the wires, the free surface of the liquid is distorted;
   means for generating a signal corresponding to the distortion in the free surface of the liquid positioned above the coating; and
   means for processing the signal to determine the properties of the liquid.

2. The apparatus of claim 1 wherein said means for generating a signal corresponding to the distortion in the free surface of the liquid is a CCD camera.

3. A method of determining viscosity of a liquid comprising:
   moving a transparent support at a speed, s, having a liquid on the topside of the support, the liquid having a free surface and a thickness, d;
   positioning an electrostatic leveler above the free surface of the liquid which includes:
      a plurality of spaced apart wires extending in a direction parallel to the movement of the support;
      applying a voltage to the spaced apart wires which produces an electric field amplitude $E_f$ at the free surface, with an amplitude of the variation of the square of the electric field at the free surface represented by $\Delta(E_f^2)$, thereby creating a disturbance having an amplitude $\Delta\delta_{FS}$ in the free surface of the liquid at a distance Z from the beginning of the wires; and
   determining the viscosity, $\mu$ of the liquid according to the equation:

$$\mu = \frac{d^3 \epsilon_0 Z}{6s\Delta\delta_{FS}} \left( \frac{2\pi}{\lambda} \right)^2 \Delta(E_f^2)$$

wherein
   $\epsilon_0$ is the dielectric constant of air; and
   $\lambda$ is the wavelength of the disturbance in a direction perpendicular to the movement of the support.

4. A method for determining surface tension of a liquid comprising:
   moving a transparent support at a speed, s, having a liquid on the topside of the support, the liquid having a free surface and a thickness, d;
   positioning an electrostatic leveler above the free surface of the liquid which includes:
      a plurality of spaced apart wires extending in a direction parallel to the movement of the support;
      applying a voltage to the spaced apart wires which produces a disturbance having an amplitude $\Delta\delta_{FS\infty}$ in the free surface at a nearly periodic electric field applied at the free surface $E_f$ with the amplitude of the square of its variations $\Delta(E_f^2)$ thereby creating a disturbance having an amplitude $\Delta\delta_{FS\infty}$ in a free surface at a distance Z sufficiently far from where the liquid enters the test section so that the distortion is no longer changing;

determining the surface tension of 6 of the liquid according to the equation:

$$\sigma = \left(\frac{\lambda}{2\pi}\right)^2 \left(\frac{\epsilon_o \Delta(E_f^2)}{2\Delta\delta_{FS\infty}} - \rho g\right)$$

wherein $\epsilon_0$ is the dielectric constant of air;

$\rho$ is the density of the liquid; and $\lambda$ is the wavelength of the disturbance in a direction perpendicular to the motion of the support.

5. A method for determining surface dilational elasticity of a liquid comprising:

moving a transparent support at a speed s, having a liquid on the topside of the support, the liquid having a free surface and a thickness, d;

positioning an electrostatic leveler above the free surface of the liquid which includes:

a plurality of spaced apart wires extending in a direction parallel to the movement of the support;

applying a voltage to the spaced apart wires which produces a spatially non-uniform electric field $E_f$, with the amplitude of the variation of the square of the electric field represented by $\Delta(E_f^2)$, thereby creating a disturbance having an amplitude $\Delta\delta_{FS}$ in the free surface at a distance Z from where the liquid is first exposed to the wires measured in the direction of motion of the support; and determining the surface dilational elasticity by fitting the amplitude of the free surface disturbance $\Delta\delta_{FS}$ as it changes with distance to the following set of equations which contain the surface dilational elasticity e as the only unknown parameter:

$\Delta\delta_{FS} =$ $$\frac{\Delta\delta_{FS\infty}}{2} \left[ \left(1 - \frac{1+3E}{D_{disc}}\right) e^{-\kappa_1 \tau} + \left(1 + \frac{1+3E}{D_{disc}}\right) e^{-\kappa_2 \tau} - 2 \right]$$

wherein $$D_{disc} = \sqrt{(1+3E)^2 - 9E}$$

$$\kappa_1 = \frac{-3E + 1 - D_{disc}}{6}$$

$$\kappa_2 = \frac{-3E + 1 + D_{disc}}{6}$$

$$E = \frac{e}{d^2} \cdot \frac{1}{\left[\rho g + \sigma\left(\frac{2\pi}{\lambda}\right)^2\right]}$$

$$\tau = \frac{d^3}{\mu s} \left(\frac{2\pi}{\lambda}\right)^2 \left[\rho g + \sigma\left(\frac{2\pi}{\lambda}\right)^2\right] Z$$

and e=2.718282 . . . is the base of the exponential function; $\Delta\delta_{FS}$ and $\Delta\delta_{FS\infty}$ are, respectively, the displacement of the free surface at each position Z and sufficiently far form where the coating is initially subjected to the electrostatic field so that the disturbance no longer changes;

$\rho$, $\mu$ and $\sigma$ are, respectively, the density and viscosity of the liquid and the surface tension at the free surface between the liquid and the air;

g is the gravitational constant;

$\lambda$ is the wavelength of the disturbance which coincides with the separation of the wires, these wires being aligned with the direction of motion of the moving support; and e is the surface dilational elasticity in kg/s$^2$.

6. A method for determining film coating thickness comprising:

moving a transparent support at a speed, s, having a liquid on the topside of the support, the liquid having a free surface and a thickness, d;

positioning an electrostatic leveler above the free surface of the liquid which includes:

a plurality of spaced apart wires extending in a direction parallel to the movement of the support;

applying a voltage to the spaced apart wires which produces a nearly periodic electric field applied at the free surface $E_f$, with the amplitude of the square of its variation $\Delta(E_f^2)$ thereby creating a disturbance having an amplitude $\Delta\delta_{FS\infty}$ in the free surface at a distance Z from the beginning of the wires; and determining the coating thickness of the film according to the equation:

$$d = \left\{ \frac{6\mu s \Delta\delta_{FS}/Z}{\epsilon_o \Delta(E_f^2)} \left(\frac{\lambda}{2\pi}\right)^2 \right\}^{1/3}$$

wherein $\mu$ is the viscosity of the liquid;

$\epsilon_0$ is the dielectric constant of air; and $\lambda$ is the wavelength of the disturbance coinciding with the separation of the wires.

7. A method of determining viscosity of the layers of a liquid film having multiple layers comprising:

moving a transparent support at a speed, s, having a liquid film of multiple layers on the topside of the support, and the liquid having a free surface and a thickness, d;

positioning an electrostatic leveler above the free surface of the liquid film of multiple layers which includes:

a plurality of spaced apart wires extending in a direction parallel to the movement of the support;

applying a voltage to the spaced apart wires which produces an electric field of amplitude $E_f$ at the free surface, with an amplitude of variation of the square of the field at the free surface represented by $\Delta(E_f^2)$ thereby creating a disturbance having an amplitude $\Delta\delta_{FS\infty}$ in the free surface of the liquid at a distance Z from a beginning of the wires; and first, determining the effective viscosity, $\mu_{eff}$ for the liquid of multiple layers according to the equation:

$$\mu_{eff} = \frac{d^3 \epsilon_o Z}{6s\Delta\delta_{FS}} \left(\frac{2\pi}{\lambda}\right)^2 \Delta(E_f^2)$$

wherein $\epsilon_0$ is the dielectric constant of air, $\lambda$ is the wavelength of the disturbance in the plane of the support but perpendicular to the movement of the support; and second, determining the viscosity of $\mu_i$ of each layer i of the n layers in the film by measuring the amplitude $\Delta\delta_i$ of the thickness variation of each layer i by solving (by matrix inversion) the following set of n equations that are linear in the unknowns $1/\mu_i$:

$$\sum_{j=1}^{i-1} \frac{D_{ij}}{\mu_j} + \frac{1}{\mu_i} \int_{y_{i-l}}^{y_i} \left[ \int_{y_{i-l}}^{y'} (d-y'')dy'' \right] dy' = \frac{\Delta \delta_i}{\Delta \delta_{FS}} \frac{d^3}{3\mu_{eff}} \text{ for } i=1, 2, \ldots, n$$

wherein $$\sum_{j=1}^{i-1} \frac{D_{ij}}{\mu_j} = 0 \text{ in the case of } i=1;$$

$\Delta \delta_i$=amplitude of the thickness disturbance of the $i^{th}$ layer;

$\mu_i$=viscosity of the $i^{th}$ layer;

$\mu_j$=viscosity of layers below the $j^{th}$ layer;

$y_i$=upper interface of the $i^{th}$ layer; and n=number of layers.

8. A method of determining surface dilational elasticity of coatings of multiple layers comprising:

moving a transparent support at a speed, s, having a liquid of multiple layers on the topside of the support, the liquid having a free surface and a thickness, d;

positioning an electrostatic leveler above the free surface of the liquid of multiple layers which includes:

a plurality of spaced apart wires extending in a direction parallel to the movement of the support;

applying a voltage to the spaced apart wires which produces a spatially non-uniform electric field $E_f$, with the amplitude of the variation of the square of the electric field represented by $\Delta(E_f^2)$, thereby creating a disturbance having an amplitude $\Delta \delta_{FS}$ in the free surface of the liquid at a distance Z from where the liquid is first exposed to the wires measured in the direction of motion of the support; and determining the surface dilational elasticity by fitting the amplitude of the free surface disturbance $\Delta \delta_{FS \infty}$ as it changes with distance to the following set of equations which contain the surface dilational elasticity e as the only unknown parameter:

$$\Delta \delta_{FS} = \left[ \frac{\delta_o f}{4L^2} \right] \frac{V_o^2}{\left\{ \rho g + \sigma \left( \frac{2\pi}{\lambda} \right)^2 \right\}} \left[ 2 - \left( 1 - \frac{I_2 + 3I_0 E}{D_{disc}} \right) e^{-\kappa_1 \tau} - \left( 1 + \frac{I_2 + 3I_0 E}{D_{disc}} \right) e^{-\kappa_2 \tau} \right]$$

wherein $$I_j = \frac{\mu_1}{d^{j+1}} \sum_{i=1}^{n} \frac{(y_i^{j+1} - y_{i-1}^{j+1})}{\mu_i} \text{ wherein } j=0, 1 \text{ or } 2$$

$$D_{disc} = \sqrt{(I_2 + 3I_0 E)^2 - 9I_1^2 E}$$

$$\kappa_1 = \frac{-3I_0 E + I_2 - D_{disc}}{6}$$

$$\kappa_2 = \frac{-3I_0 E + I_2 + D_{disc}}{6}$$

$$\tau = \frac{d^3}{\mu_1} \left( \frac{2\pi}{\lambda} \right)^2 \left[ \rho g + \sigma \left( \frac{2\pi}{\lambda} \right)^2 \right] \frac{Z}{s}$$

$\rho$=density;

$\mu_i$=viscosity of the $i^{th}$ layer;

$\sigma$=surface tension;

g=gravitational constant; and $\lambda$=wavelength of the disturbance which coincides with the separation of the wires.

* * * * *

UNITED STATES PATENT AND TRADEMARK OFFICE
CERTIFICATE OF CORRECTION

PATENT NO.: 5,590,560
DATED: January 7, 1997
INVENTOR(S): Felipe M. Joos and Alfred K. Anders

It is certified that error appears in the above-identified patent and that said Letters Patent is hereby corrected as shown below:

Column 20, line 67 through column 21, line 1, delete "a disturbance having an amplitude $\Delta\delta_{FS\infty}$ in the free surface at".

Column 21, line 4, "a free" should read --the free-- ; and line 8, "6" should read -- $\sigma$ --.

Column 23, line 12, after "wherein" insert the formula $$-- D_{ij} = (y_i - y_{i-1}) \int_{y_{j-1}}^{y_j} (d - y') dy' ; --.$$

Signed and Sealed this

Eighth Day of July, 1997

Attest:

BRUCE LEHMAN

*Attesting Officer*  *Commissioner of Patents and Trademarks*